(12) United States Patent
Li et al.

(10) Patent No.: US 8,147,672 B2
(45) Date of Patent: Apr. 3, 2012

(54) PROCESS FOR THE PREPARATION OF SUCRALOSE

(75) Inventors: Shaoxiong Li, Guangdong (CN); Ziang Chen, Guangdong (CN); Patrick Deng, Guangzhou (CN)

(73) Assignee: Techno Food Ingredients Co., Ltd., Fujian (CN)

( * ) Notice: Subject to any disclaimer, the term of this patent is extended or adjusted under 35 U.S.C. 154(b) by 0 days.

(21) Appl. No.: 13/051,959

(22) Filed: Mar. 18, 2011

(65) Prior Publication Data

US 2011/0168568 A1 Jul. 14, 2011

Related U.S. Application Data

(62) Division of application No. 11/487,711, filed on Jul. 17, 2006, now Pat. No. 7,910,727.

(30) Foreign Application Priority Data

Apr. 3, 2006 (CN) .......................... 2006 1 0034731

(51) Int. Cl.
*C25B 3/00* (2006.01)
*C07H 1/00* (2006.01)

(52) U.S. Cl. .................... 205/421; 205/427; 536/124

(58) Field of Classification Search .............. 205/421, 205/427; 536/124
See application file for complete search history.

(56) References Cited

U.S. PATENT DOCUMENTS

| | | | |
|---|---|---|---|
| 4,362,869 A | 12/1982 | Jenner et al. | |
| 4,380,476 A | 4/1983 | Mufti et al. | |
| 4,783,526 A | 11/1988 | O'Brien et al. | |
| 4,801,700 A | 1/1989 | Tully et al. | |
| 4,889,928 A | 12/1989 | Simpson | |
| 4,950,746 A | 8/1990 | Navia | |
| 4,980,463 A | 12/1990 | Walkup et al. | |
| 5,023,329 A | 6/1991 | Neiditch et al. | |
| 5,089,608 A | 2/1992 | Walkup et al. | |
| 2005/0173255 A1* | 8/2005 | Bokisa et al. | ............... 205/255 |
| 2005/0189231 A1* | 9/2005 | Capper et al. | ............... 205/246 |

FOREIGN PATENT DOCUMENTS

| | | |
|---|---|---|
| EP | 0475619 A | 3/1992 |
| EP | 0776903 A | 6/1997 |
| GB | 1543167 | 3/1979 |
| GB | 1543168 | 3/1979 |
| GB | 2079749 A | 1/1982 |
| GB | 2145080 A | 3/1985 |
| WO | WO 2004/104016 A1 | 12/2004 |

OTHER PUBLICATIONS

Tang Zhen-Xing, Shi Lu-er (College of Chemical Engineering and Materials Science, Zhejiang University of Technology, Hangzhou 310014,China), Research Progress in Preparation of Trichlorosucrose, Dec. 2005, 6 pages.

Ling M, et al. "Study on Preparation of High-Intensity Sweetener—Trideoxygalactosucrose by Monoesterification" Food Science 2002 vol. 5 No. 23: pp. 51-54.

U.S. Appl. No. 11/487,711, Selected pages from Image File Wrapper dated Apr. 7, 2010 through Nov. 17, 2010, 36 pages.

* cited by examiner

*Primary Examiner* — Edna Wong
(74) *Attorney, Agent, or Firm* — Lathrop & Gage LLP

(57) ABSTRACT

A process for preparing sucrose-6-ester is provided, which comprises electrolyzing an electrolyte solution containing sucrose, an acylating reagent and a halide catalyst. Also disclosed is a process for preparing sucralose, which involves the preparation and chlorination of sucrose-6-ester followed by deacylation of the molecule. The process of the invention can be more readily performed with a higher yield than those in the art.

19 Claims, 1 Drawing Sheet

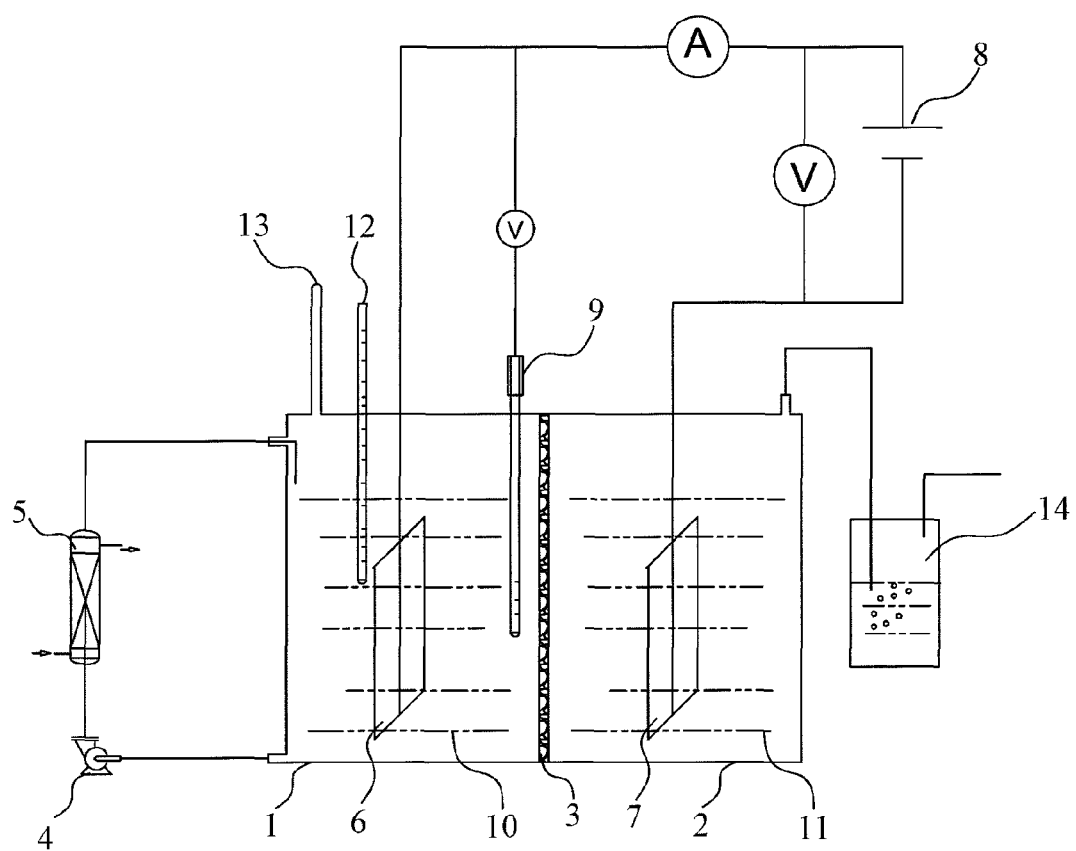

PROCESS FOR THE PREPARATION OF SUCRALOSE

RELATED APPLICATION

This application is a Divisional of U.S. application Ser. No. 11/487,711, filed Jul. 17, 2006, now U.S. Pat. No. 7,910,727, which claims priority to Chinese Patent Application 200610034731.3, filed Apr. 3, 2006. The disclosures of the aforementioned applications are incorporated herein by reference.

BACKGROUND OF THE INVENTION

1. Technical Field of the Invention

The present invention relates to a process for the preparation of sucrose-6-ester and, hence, the preparation of the intensive sweetener sucralose.

2. Description of Prior Art

Sucralose, namely 4,1',6'-trichloro-4,1',6'-trideoxy galactosucrose or 1,6-dichloro-1,6-dideoxy-β-D-fructofuranosyl 4-chloro-4-deoxy-α-D-galactopyranoside (formula I), is a intensive sweetener having a sweetness several hundred times that of sucrose. Its use as a sweetener and sweetening compositions containing it are disclosed in British Patent Specification No. 1,543,167.

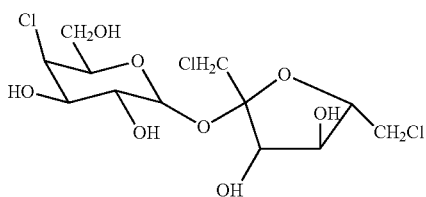

I

Sucralose is derived from sucrose by replacing the hydroxyls at the 4-, 1'-, and 6'-positions with chlorine, in which the stereo configuration at the 4 position is reversed. The major problem in the synthesis of sucralose concerns the chlorination of the 4-, 1'- and 6'-positions of a sucrose molecule without chlorination at other positions.

One way of achieving this is to chlorinate a sucrose derivative having the 2-, 3-, 6-, 3'- and 4'-positions blocked, conveniently by esterification, so that only the 4-, 1'- and 6'-positions are available for chlorination. Such a method is also referred to as a "full-protection method", since all positions not to be chlorinated are protected (see, for example, U.S. Pat. Nos. 4,801,700; 4,783,526 and 4,362,869, which are explicitly incorporated herein by reference in their entirety). However, the full-protection method is complicated and has technical difficulties in selectively protecting the five positions not to be chlorinated.

In addressing the above issue, recently, a "single-protection method" has been recommended and employed in practice, which involves selective chlorination of a sucrose-6-ester (formula II) at the 4-, 1'- and 6'-positions, followed by deacylation to provide sucralose. Examples of such methods can be found, for example, in U.S. Pat. Nos. 4,950,746; 5,023,329 and 5,089,608, EP 0,475,619A; EP 0,776,903A and GB 2,145,080A, which are explicitly incorporated herein by reference in their entirety.

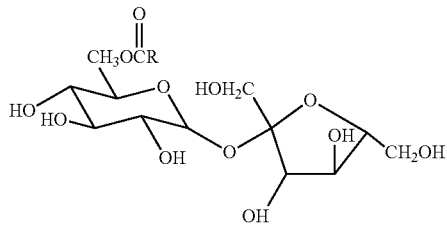

II

The single-protection method is based on the discovery that hydroxyls at different positions of sucrose differ in reactivity. For example, the chlorinating reactivity of these hydroxyls decreases orderly as 6, 6'>4>1'>others (see P. H. Fairclough, et. al, Carbohydr. Res., 40,285 (1975); L. Hough, et. al., and GB 1,543,167 and GB 1,543,168 (1979)). Therefore, if the most reactive 6-hydroxyl group is protected with an acyl group, a sucrose-6-ester can be readily converted into sucralose by replacing the more reactive hydroxyls at the 4-, 1'- and 6'-positions with chlorine and then recovering the 6-hydroxyl group.

Formation of a sucrose-6-ester is of the most importance to the single-protection method. Philip J. Simpson, in U.S. Pat. No. 4,889,928, discloses a method of preparing a sucrose-6-ester, which comprises reacting sucrose with a trialkyl orthoacrylate to give a sucrose alkyl 4,6-orthoacylate, hydrolyzing the 4,6-orthoacylate and isomerizing the resulting mixture to provide the desired sucrose-6-ester. This method is complicated, difficult to operate, and low in yield. David S, Neiditch et al., in U.S. Pat. No. 5,023,329, disclose an alternative method of preparing a sucrose-6-ester, which comprises reacting sucrose with a di(hydrocarbyl)tin oxide to produce an organotin-sucrose adduct, which can be readily acylated in situ to afford the sucrose-6-ester. This method is highly selective and more efficient, however it also has disadvantages that a di(hydrocarbyl)tin oxide is needed, of which the regeneration is very complicated, and that the tin compound used is hazardous. An enzymatic method is disclosed in GB 2,145,080A for the preparation of a sucrose-6-ester, which is highly selective, high in yield, and may be performed in mild conditions. However, the screening and processing of an enzyme suitable in this method is quite difficult. As a result, no industrial application of the enzymatic method has been reported till now.

A key step in the synthesis of sucralose is the chlorination of sucrose derivatives, of which various processes have been reported. For example, Water A. Szarek, in Advances in Carbohydrate Chemistry & Biochemistry 28, 225-307 (1973), discloses the preparation of halogenated deoxy-sucrose using various chlorinating reagents; Viehe, et. al., in Angew. Chem. Internal. Edit 12 (10), 808-818 (1979), disclose the chlorination of alcohols with a Vilsmeier reagent obtained by reacting DMF with carbonyl chloride; and Eilingsfeld et al., in Angew. Chem. 72(22), 836-845, (1960), disclose the preparation of Vilsmeier reagents by reacting various chlorine-containing agents with tertiary amides. These studies have provided a theoretical base for the preparation of sucralose. Walkup, et al., in U.S. Pat. No. 4,980,463, disclose a method for chloration of sucrose-6-ester, characterized in that a chloroformiminium chloride salt (a Vilsmeier reagent) obtained by reacting DMF with carbonyl chloride is used as the chlorinating reagent, and DMF is also used as the solvent for chlorination. However, carbonyl chloride is highly poisonous, which may bring inevitably problems to industrial applications. In addition, DMF is miscible with water and many conventional organic solvents, which makes it complicated and inefficient to separate desired products from the resulting chlorinated mixture containing substantive inorganic salts and various organic components by extraction with solvents.

BRIEF SUMMARY OF THE INVENTION

The present invention provides an economical and efficient process for preparing sucrose-6-ester, which can be more readily performed with a higher yield than those in the art. Also provided is a process for preparing sucralose, which is highly selective and more productive.

According to an aspect of the present invention, there is provided a process for the preparation of sucrose-6-ester comprising electrolyzing an electrolyte solution containing sucrose, an acylating reagent and a halide catalyst.

The process of the invention is preferably carried out in an electrolysis system comprising an anode electrolyte solution containing sucrose, the acylating reagent and the halide catalyst, and a cathode electrolyte solution. Preferably, the cathode electrolyte solution is an aqueous solution of sodium chloride.

A preferred acylating reagent of the invention is an aldehyde, especially an alkyl aldehyde or an arylalkyl aldehyde. Preferably, the aldehyde may be selected from the group consisting of formaldehyde, acetaldehyde, propaldehyde, and benzaldehyde, more preferably is acetaldehyde or benzaldehyde.

Preferably, the halide catalyst used is a chloride, bromide or iodide, more preferably a chloride or bromide, and still more preferably an alkali metal chloride or bromide, such as KCl and KBr.

According to a further aspect of the present invention, there is provided a process for the preparation of sucralose comprising the steps of:

(i) electrolyzing an electrolyte solution containing sucrose, an acylating reagent and a halide catalyst to produce a sucrose-6-ester;
(ii) chlorinating the sucrose-6-ester to form a 4,1',6'-trichlorinated sucrose-6-ester; and
(iii) hydrolyzing the 4,1',6'-trichlorinated sucrose-6-ester to provide sucralose.

The chlorating reagent used in step (ii) is preferably selected from the group consisting of sulphuryl chloride, thionyl chloride, phosphorus trichloride, phosphorus oxychloride, phosphorus pentachloride, oxalyl chloride, methane sulfonyl chloride and carbonyl chloride, and more preferably is sulphuryl chloride or thionyl chloride.

BRIEF DESCRIPTION OF THE DRAWINGS

FIG. 1 is a sketch diagram illustrating the structure and the working principle of an electrolysis bath used in examples.

DETAILED DESCRIPTION OF THE INVENTION

In a first aspect of the present invention, there is provided a process for the preparation of sucrose-6-ester comprising electrolyzing an electrolyte solution containing sucrose, an acylating reagent and a halide catalyst.

According to a particular embodiment of the invention, the process is performed in an electrolysis system comprising an anode electrolyte solution containing sucrose, the acylating reagent and the halide catalyst, and a conventional cathode electrolyte solution such as an aqueous sodium chloride solution.

In a preferred embodiment of the invention, the acylating reagent used is an aldehyde, especially an alkyl aldehyde or an arylalkyl aldehyde. Preferably, the aldehyde is selected from the group consisting of formaldehyde, acetaldehyde, propaldehyde and benzaldehyde, and more preferably is acetaldehyde or benzaldehyde. The amount of the acylating reagent used is preferably about 1.0 to 2.5 times the amount of sucrose in mole, more preferably 1.2 to 1.5 times.

In another preferred embodiment of the invention, the halide catalyst used is a chloride, bromide or iodide, preferably is a chloride or bromide, and more preferably is an alkali metal chloride or bromide, such as KCl and KBr.

Without wishing to be bound by any particular theory, there is provided herein a hypothesis of the electrolysis process for better understanding of the invention. In an embodiment where an aldehyde is used, the halogen ion (X—) in the anode electrolyte solution is firstly converted into a hypohalous acid (HXO), which is highly oxidative and unstable. Then, the aldehyde reacts with the HXO to form a carbonyl carbocation, which is more potent as an acylating agent, and at the same time the HXO is reduced back to X—. After that, the carbocation reacts with the 6-hydroxyl of sucrose to form a sucrose-6-ester. The major reactions taking place in the anode electrolyte solution during the electrolysis of step (i) are listed as follows:

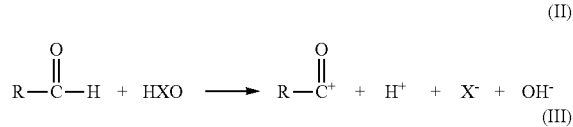

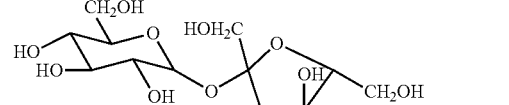

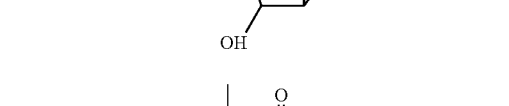

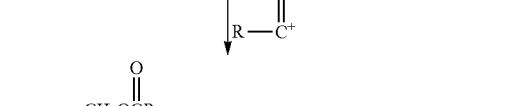

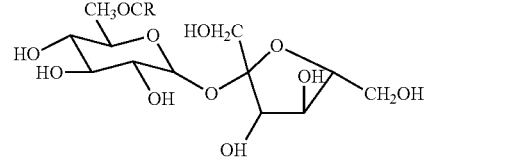

wherein X is halogen and R is alkyl or arylalkyl.

As shown above, the halide catalyst used is consumed in Reaction I, and then regenerated in Reaction II while preparing the sucrose-6-ester. Therefore, no additional process is needed to separate and regenerate the halide catalyst.

A full electrochemical process is generally composed of an anode process induced by an anode potential and a cathode process induced by a cathode potential. Since the aldehyde used in the present invention may be reduced to its corresponding alcohol, which then may react with the carbonyl carbocation to form an ester, under a cathode potential, the anode electrolyte solution should be separated from the cathode solution to avoid the effect of the cathode potential to the reactants in the anode solution.

In a preferred embodiment of the invention, a non-selective film having excellent ion permeability is used to separate the anode solution and the cathode solution, and thereby the reactants and products in each solution are separated respectively. As a result, undesired side reactions are reduced and the separation of target products is simplified. The non-selective film used in the invention may be a microporous ceramic film or a glass film having excellent ion permeability.

The solvent used in the anode electrolyte solution of the invention may be any solvent that is miscible with water and suitable for an electrolyte solution, and in which sucrose is soluble. Examples of the solvent used comprise, but not limited to, N,N-dimethylformamide (DMF), N,N-diethylformamide, N,N-dimethylacetamide, ketones, acetonitrile and aromatic solvents, of which N,N-dimethylformamide is preferred. The amount of the solvent is preferably about 5 to 30 times that of sucrose. Water is not suitable as the solvent, because the aldehyde will be converted into a carboxylic acid, which is less active as an acylating agent, in the presence of HXO and water. Furthermore, the yield and selectivity of the esterification of sucrose decreases in water, and thereby the amount of by-products and the difficulty for separation of products increase. However, there should be a certain amount of water in the anode electrolyte solution, because water is necessary for the formation of HXO and, in addition, the conductivity of the electrolyte solution and the reaction rate increase in the presence of water. Therefore, it is important to control the concentration of water in the anode electrolyte solution, which should be maintained in the range of about 0.1% to 10%, preferably about 0.5% to 5%. The concentration of water may be monitored using Karl Fischer titration method during the electrolysis.

Control of the anode potential is also important for the electrolysis for the reason that several electrode reactions may take place under different potentials for X—. Therefore, the potential should be well controlled to avoid undesired reactions. Preferably, a potentiostatic method may be used during the electrolysis, in which the anode potential (vs. SCE) is maintained at about 0.3~0.8V above the standard electrode potential of the redox couple X—/XO— to induce the desired electrode reaction (Reaction I) and keep it stable. For example, it is well known that the standard electrode potential of Cl—/ClO— is 0.89V and the standard electrode potential of Br—/BrO— is 0.76V. If the potential is too low, the reaction rate would be unacceptably low. However, if the potential is too high, the electrode reaction would become too fast, and the concentration of XO— will increase, which may deteriorate the selectivity of the esterification of sucrose.

The concentration of X— in the anode solution also affects the concentration of XO—, and therefore it is also important for the selectivity of esterification. Preferably, the concentration of the halide catalyst is controlled at about 0.5% to 10%, more preferably at about 1% to 5%.

A reactive temperature is also a factor affecting the selectivity. Preferably, the temperature is controlled at about −5° C. to 50° C., more preferably at about 5° C. to 20° C. If the temperature is higher than 50° C., the selectivity will be deteriorated. But if the temperature is lower than −5° C., the dissolvability of sucrose decreases, which may increase the amount of the aldehyde acidified. To avoid the increase of temperature caused by the electrode reactions, a circulating heat-exchange method can be applied to keep the temperature of the anode electrolyte solution within the desired bounds.

Since the dissolvability of the halide catalyst is low in an organic solvent like DMF and the like, an additional supporting electrolyte may be added to the anode electrolyte solution to increase the conductivity of the solution and accelerate the reaction. Examples of the supporting electrolyte used comprise, but are not limited to, quaternary ammonium salts and lithium salts of fluoboric acid and perchloric acid, tetraalkylammonium, tetrachloro-borate and sulfonate. The amount of the supporting electrolyte is about 0.1% to 15% by weight based on the total weight of the electrolyte solution, preferably about 0.2% to 3% by weight.

In addition, a stable cathode electrode reaction is also beneficial to the stability of the anode electrode reactions. A most simple and stable cathode electrode reaction is the electrolysis reaction of an aqueous solution of sodium chloride, of which the product at the cathode is hydrogen.

In an embodiment of the invention, the electrolysis of the process may be monitored by measuring the concentration of sucrose using thin-layer chromatography. The electrolysis is stopped when the sucrose is depleted. The electrolyzed anode solution is then neutralized by an alkali solution and evaporated to remove the solvent. The resulted residue is recrystallized, washed and dried to afford the sucrose-6-ester.

According a second aspect of the invention, there is provided a process for the preparation of sucralose comprising the steps of:
 (i) electrolyzing an electrolyte solution containing sucrose, an acylating reagent and a halide catalyst to produce a sucrose-6-ester;
 (ii) chlorinating the sucrose-6-ester to form a 4,1',6'-trichlorinated sucrose-6-ester; and
 (iii) hydrolyzing the 4,1',6'-trichlorinated sucrose-6-ester to provide sucralose.

In an embodiment of the invention, the chlorating reagent used in step (ii) may be selected from the group consisting of sulphuryl chloride, thionyl chloride, phosphorus trichloride, phosphorus oxychloride, phosphorus pentachloride, oxalyl chloride, methane sulfonyl chloride and carbonyl chloride, and preferably is sulphuryl chloride or thionyl chloride.

In another embodiment of the invention, step (ii) is carried out in a polar organic solvent having a boiling point over 120° C., which is immiscible with water and has good dissolvability to sucrose-6-ester. Preferably, the solvent may be selected from the group consisting of butyl acetate, hexyl acetate, cyclohexanone and 1,1,2,2-tetrachloroethane, and more preferably is butyl acetate or 1,1,2,2-tetrachloroethane.

In still another embodiment of the invention, to improve the selectivity of the chlorination, step (ii) is carried out in the presence of a chlorination catalyst selected from the group consisting of pyridines including pyridine and alkyl substituted pyridine, and tertiary amides such as dimethylalkylamide and dialkylformamide. Preferably, the chlorination catalyst is selected from the group consisting of N,N-dimethylformamide, N,N-diethylformamide and pyridine, and more preferably is N,N-dimethylformamide or pyridine. While not wishing to be bound by any particular theory, the inventors believe that in case a pyridine is used, the pyridine may act as a solvent for the reactants, as an acid acceptor for the hydrogen chloride released and as a catalyst for the release of chloride ions for the last stage of the reaction. In case a tertiary amide is used, the amide may form a chloroformiminium chloride salt (a Vilsmeier reagent) with the chlorinating reagent used.

In a particular embodiment of the invention, the chlorinating reagent is added dropwise to the solution of sucrose-6-ester and tertiary amide at a temperature of below 10° C. After the addition, the reaction mixture is heated to about 115° C. in 2 hours and maintained at the temperature for 30 minutes.

In a preferred embodiment of the invention, the trichlorosucrose-6-ester from step (ii) is hydrolyzed in the presence of an alkali to remove the acyl group at the 6 position, followed by neutralization, extraction, condensation and crystallization to afford the desired sucralose.

In a further preferred embodiment of the invention, the hydrolysis of the trichloro-sucrose-6-ester is carried out at pH 9-11 using a strong base anion exchange resin column to adsorb the acyl anion formed and release hydroxyl to maintain the pH of the reaction solution.

Hereinafter, the invention will be illustrated more in detail by the following examples with reference to the drawings for better understanding of various aspects and advantages of the invention. However, it should be understood that the examples below are non-limiting and are only illustrative of some of the embodiments of the present invention.

EXAMPLES

Apparatus

FIG. 1 illustrates an electrolysis system used in the process of the present invention, which comprises an anode chamber 1 having an anode 6 and a cathode chamber 2 having a cathode 7 separated from each other by a microporous ceramic film 3. A circulating pump 4 and a heat-exchanger 5 are provided to remove heat from an anode electrolyte solution 10 in the anode chamber to control the temperature therein, which is monitored with a thermometer 12. The anode 6 may be an electrode of platinum or other heavy metals or a graphite electrode, and the cathode 7 is an electrode of stainless steel sheet. The electrolytic potential is provided by a regulated alternating-current/direct-current transformer 8, of which the output potential is up to 24V and the output power is up to 5 KW. The anode potential is measured versus a saturated calomel electrode (SCE) 9.

The following Examples 1-8 are provided with reference to FIG. 1.

Preparations of Sucrose-6-Esters

Example 1

N,N-dimethylformamide (12 L, 99.5%) and distilled water (50 mL) were added into the anode chamber 1, to which sucrose (1000 g, 2.92 mol), acetaldehyde (150 g), potassium bromide (50 g) and $(Et)_4NBF4$ (25 g) were then added. The circulating pump 4 was initiated to help mixing and dissolution of the components. A proper amount of aqueous solution of sodium chloride (10%) was added to the cathode chamber 2 as a cathode electrolyte solution 11.

The temperature in the anode chamber was adjusted to 15° C. by the heat-exchanger 5, and the transformer 8 was regulated to maintain an anode potential of 1.1V (vs. SCE). The electrolysis rate was estimated by observing bubbles of hydrogen generated in the cathode chamber and collected by a hydrogen collector 14. The current intensity applied was recorded, and the concentration of sucrose in the electrolyte solution was monitored using thin-layer chromatography. At the beginning of the electrolysis, some sucrose remained undissolved in the anode chamber 1, which then diminished gradually during the electrolysis. The electrolysis was stopped when all sucrose was depleted.

The electrolyzed mixture in the anode chamber was neutralized using a 2N solution of $NaCO_3$ and then evaporated under vacuum to remove the solvent, providing a dark red syrup. The syrup was dissolved in a 1,000 mL anhydrous methanol with heating. After being cooled to room temperature, 2 g of a seed crystal of sucrose-6-ester was added to the solution, which was then cooled gradually to 10° C. and kept over night at the temperature. The crystal formed was filter off, washed with a small amount of cold methanol, and dried under vacuum to yield 437 g crude sucrose-6-acetate, which comprises sucrose-6-acetate 83.6%, sucrose-4-acetate 5.2%, sucrose-di-acetate 1.8% and sucrose 1.6%. The mother liquor after crystallization was evaporated to remove methanol, and the $(Et)_4NBF4$ in the residue was recovered for reuse.

Example 2

A sucrose-6-ester was prepared in the same manner as described in Example 1, except that 50 g of potassium chloride was used in place of potassium bromide and the anode potential was maintained at 1.32V (vs. SCE).

The electrolyzed mixture was neutralized and evaporated under vacuum to provide a dark red syrup. The syrup was dissolved in hot methanol (1,200 mL), allowed to cool to 10° C. and kept over night. The crystal separated out was collected and purified to afford 417 g of crude sucrose-6-acetate.

Analysis of the crude sucrose-6-acetate with liquid chromatography: sucrose-6-acetate 78.65%, sucrose-4-acetate 6.2%, sucrose-diacetate 2.3% and sucrose 1.1%.

Example 3

A sucrose-6-ester was prepared in the same manner as described in Example 1, except that 375 g benzaldehyde was used in place of acetaldehyde and 50 g of $(n-Bu)_4NCl_4$ was used instead of $(Et)_4NBF_4$.

The electrolyzed mixture was neutralized and evaporated under vacuum to provide a dark red syrup. The syrup was dissolved in acetone (2,000 mL) at 50° C. with stirring, allowed to cool to room temperature and then seeded with a crystalline of sucrose-6-benzoate (3 g). Crystallization was allowed to proceed overnight and the product was collected, washed with a small amount of acetone and dried under vacuum to afford 526 g of crude sucrose-6-benzoate.

Analysis of the crude product with liquid chromatography: sucrose-6-benzoate 83.1%, sucrose-4-benzoate 4.3%, sucrose-dibenzoate 0.75% and sucrose 1.9%.

Example 4

Sucrose-6-ester was prepared in the same manner as described in Example 1, except that 375 g benzaldehyde was used in place of acetaldehyde, 50 g of potassium chloride was used instead of potassium bromide, and the anode potential was maintained at 1.32V (vs. SCE).

The electrolyzed mixture was neutralized and evaporated under vacuum to provide a dark red syrup. The syrup was dissolved in acetone (2,000 mL) at 50° C. with stirring, allowed to cool to room temperature and then seeded with a crystalline of sucrose-6-benzoate (3 g). Crystallization was allowed to proceed overnight and the product was collected, washed with a small amount of acetone and dried under vacuum to afford 513 g crude sucrose-6-benzoate.

Analysis of the crude product with liquid chromatography: sucrose-6-benzoate 81.9%, sucrose-4-benzoate 4.1%, sucrose-dibenzoate 0.94% and sucrose 2.3%.

Example 5

A sucrose-6-ester was prepared in the same manner as described in Example 1, except that 500 mL distilled water was used.

The electrolyzed mixture was neutralized and evaporated under vacuum to provide a dark red syrup. The syrup was dissolved in hot methanol (1200 mL), allowed to cool to room temperature, seeded with a crystalline of sucrose-6-acetate, and further cooled to 10° C. Crystallization was allowed to proceed overnight and the product was collected, washed and dried under vacuum to afford 542 g crude sucrose-6-acetate.

Analysis of the crude product with liquid chromatography: sucrose-6-acetate 42%, sucrose-4-acetate 16.3%, sucrose-6'-acetate 5.7%, sucrose-diacetate 0.17% and sucrose 39.8%.

Example 6

A sucrose-6-ester was prepared in the same manner as described in Example 1, except that 12 L of N,N-dimethylacetamide (99.5%) was used in place of DMF.

The electrolyzed mixture was neutralized and evaporated under vacuum to provide a dark red syrup. The syrup was dissolved in hot methanol (1,200 mL), allowed to cool to room temperature, seeded with a crystalline of sucrose-6-acetate, and further cooled to 10° C. Crystallization was allowed to proceed overnight and the product was collected, washed and dried under vacuum to afford 513 g of crude sucrose-6-acetate.

Analysis of the crude product with liquid chromatography: sucrose-6-acetate 82.1%, sucrose-4-acetate 4.5%, sucrose-diacetate 1.6% and sucrose 0.9%.

Example 7

A sucrose-6-ester was prepared in the same manner as described in Example 1, except that 100 g of potassium bromide was used.

The electrolyzed mixture was neutralized and evaporated under vacuum to provide a dark red syrup. The syrup was dissolved in hot methanol (1,200 mL), allowed to cool to room temperature, seeded with a crystalline of sucrose-6-acetate, and further cooled to 10° C. Crystallization was allowed to proceed overnight and the product was collected, washed and dried under vacuum to afford 519 g of crude sucrose-6-acetate.

Analysis of the crude product with liquid chromatography: sucrose-6-acetate 74.3%, sucrose-4-acetate 9.5%, sucrose-diacetate 3.1% and sucrose 0.7%.

Example 8

A sucrose-6-ester was prepared in the same manner as described in Example 1, except that 100 g of potassium bromide was used and the anode potential was maintained at 1.4V (vs. SCE).

A small amount of brown gas (bromine) released from an anode vent-pipe 13 was observed during the electrolysis. After the electrolysis was completed, the electrolyzed mixture was neutralized and evaporated under vacuum to provide a dark red syrup. The syrup was dissolved in hot methanol (1,200 mL), allowed to cool to room temperature, seeded with a crystalline of sucrose-6-acetate, and further cooled to 10° C. Crystallization was allowed to proceed overnight and the product was collected, washed and dried under vacuum to afford 519 g of crude sucrose-6-acetate.

Analysis of the crude product with liquid chromatography: sucrose-6-acetate 62.7%, sucrose-4-acetate 17.9%, sucrose-diacetate 7.3% and sucrose 0.4%.

Preparations of Trichloro-Sucrose-6-Esters

Example 9

Sucrose-6-acetate (200 g, 0.5 mol, 95%), butyl acetate (1,500 mL) and pyridine (100 mL) were added to a 3 L four-necked flask provided with a magnetic stirrer, a reflex condenser, a constant pressure separating funnel and a thermometer, stirred, and then cooled to −15° C. in a brine bath. $SO_2Cl_2$ (480 g, 3.5 mol) was then added at a temperature of no more than 5° C. After the addition, the reaction mixture was heated to 112±2° C. in an oil bath in two hours, and kept at the temperature for 30 minutes.

The oil bath was removed, and the mixture was allowed to cool to the room temperature and then further cooled to about 0° C. in a cold brine bath. To the mixture was added a 5N solution of NaOH with vigorous stirring until pH 7±0.2, while keeping at a temperature of no more than 20° C. The mixture was then transferred to a separating funnel and stood for phase separation. The aqueous phase was separated and extracted with butyl acetate (200 mL×2). The combined organic phase was washed with water (50 mL×2) and evaporated under vacuum at a temperature of below 60° C. to afford a thick syrup. Ethyl acetate (800 mL) and activated carbon (50 g) were added to the syrup, stirred for 20 minutes and filtered. The filtrate was concentrated to about 300 mL, cooled to 5° C., kept overnight, and then filtered. The residue was dried under vacuum to afford 102 g of crude trichloro-sucrose-6-acetate (purity about 86%). The trichloro-sucrose-6-acetate remained in the filtrate was about 5.3 g, and the total yield of the chlorination was about 42%. After recrystallization in ethyl acetate for three times, a fined trichloro-sucrose-6-acetate with a purity of 98% was obtained.

Example 10

Trichloro-sucrose-6-ester was prepared in the same manner as described in Example 9, except that 420 g thionyl chloride was used in place of $SO_2Cl_2$, 1,200 mL of tetrachloroethane was used in place of butyl acetate and 100 mL DMF was used instead of pyridine. 121 g of a crude trichloro-sucrose-6-acetate was obtained (purity 84.6%), and about 6.1 g of trichloro-sucrose-6-acetate still remained in the filtrate. The total yield of the chlorination was about 44.5%.

Example 11

Trichloro-sucrose-6-ester was prepared in the same manner as described in Example 9, except that 230 g sucrose-6-benzoate (96.5%) was used in place of sucrose-6-acetate, 1,200 mL of tetrachloroethane was used in place of butyl acetate. 143 g of a crude trichloro-sucrose-6-benzoate was obtained (purity 83.4%), and about 4.8 g of trichloro-sucrose-6-benzoate still remained in the filtrate. The total yield of the chlorination was about 46%.

Example 12

Trichloro-sucrose-6-ester was prepared in the same manner as described in Example 9, except that 230 g sucrose-6-benzoate (96.5%) was used in place of sucrose-6-acetate, 420 g thionyl chloride was used in place of $SO_2Cl_2$, and 100 mL DMF was used instead of pyridine. 156 g of a crude trichloro-sucrose-6-benzoate was obtained (purity 86.1%), and about 5.2 g of trichloro-sucrose-6-benzoate still remained in the filtrate. The total yield of the chlorination was about 51.6%.

Preparations of Sucralose

Example 13

Purified trichloro-sucrose-6-acetate (100 g) was dissolved in water (1,000 mL) with stirring. To the result solution was added a 5N solution of NaOH until pH 10±0.2. The solution was stirred and held at 40±2° C. in a water bath. After 15 minutes, the reaction solution was circulated through a strong base anion exchange resin (alkaline) column. The flow rate of the solution was adjusted to keep its pH between 9 and 10. The reaction mixture was termly sampled for an HPLC analysis until no sucrose 6-acetate was left (about 3 hours). Activated carbon (5 g) was then added to the reaction mixture for decoloring, and the resultant was filtered. The filtrate was subjected to a weak acid cation exchange resin column to obtain a solution of pH 6.5~7.5. The solution was then extracted with ethyl acetate (100 mL) to remove minor organic impurities. The aqueous phase was concentrated to about 180 mL which was seeded with crystalline sucralose (1 g). Crystallization was allowed to proceed overnight at 10° C. with stirring, and the product was collected and dried under vacuum to afford 53 g of sucralose (purity 99.5%).

It should be understood that although the present invention has been specifically disclosed by preferred embodiments and optional features, modification and variation of the concepts herein disclosed may be resorted to by those skilled in the art, and that such modifications and variations are considered to be falling within the scope of the invention.

What is claimed:

1. A process for the preparation of sucrose-6-ester, comprising electrolyzing an electrolyte solution comprising sucrose, an acylating reagent and a halide catalyst, wherein said electrolyzing step is carried out in an electrolysis system comprising an anode electrolyte solution and a cathode electrolyte solution, said anode electrolyte solution comprising the sucrose, the acylating reagent and the halide catalyst.

2. The process of claim 1, wherein the acylating reagent is an aldehyde.

3. The process of claim 2, wherein the aldehyde is selected from the group consisting of formaldehyde, acetaldehyde, propaldehyde, and benzaldehyde.

4. The process of claim 1, wherein the molar ratio of the acylating reagent to sucrose is about 1.0 to 2.5.

5. The process of claim 1, wherein the halide catalyst is a chloride, bromide or iodide.

6. The process of claim 1, wherein the halide catalyst is an alkali metal chloride or bromide.

7. The process of claim 1, wherein the amount of the halide catalyst is about 0.5%-10% by weight of the electrolyte solution.

8. The process of claim 1, wherein the amount of the halide catalyst is about 1%-5% by weight of the electrolyte solution.

9. The process of claim 1, wherein the electrolyte solution further contains a solvent.

10. The process of claim 9, wherein the solvent is selected from the group consisting of N,N-dimethylformamide, N,N-diethylformamide, N,N-dimethylacetamide, ketones, acetonitrile and aromatic solvents.

11. The process of claim 1, wherein the electrolyte solution further contains 0.1%-10% by weight of water.

12. The process of claim 1, wherein the electrolyte solution further contains a supporting electrolyte.

13. The process of claim 12, wherein the supporting electrolyte is selected from the group consisting of fluoboric acid quaternary ammonium salts, fluoboric acid lithium salts, perchloric acid quaternary ammonium salts, perchloric acid lithium salts, tetraalkyl-ammonium, tetrachloro-borate and sulfonate.

14. The process of claim 12, wherein the amount of the supporting electrolyte is about 0.1%-15% by weight of the electrolyte solution.

15. The process of claim 1, wherein the temperature is maintained at −5-50° C. during the electrolysis.

16. The process of claim 1, wherein said electrolyzing step is further carried out under an anode potential of about 0.3-0.8V above the standard electrode potential of the redox couple $X^-/XO^-$, wherein $X^-$ represents the halide ion from the halide catalyst.

17. The process of claim 1, wherein the anode electrolyte solution is separated from the cathode electrolyte solution by a non-selective film having excellent ion permeability.

18. The process of claim 17, wherein the non-selective film is a microporous ceramic film or a glass film.

19. The process of claim 1, wherein the cathode electrolyte solution is an aqueous solution of sodium chloride.

* * * * *